(12) United States Patent
Metz et al.

(10) Patent No.: US 7,072,435 B2
(45) Date of Patent: Jul. 4, 2006

(54) METHODS AND APPARATUS FOR ANOMALY DETECTION

(75) Inventors: Stephen W. Metz, Greenfield, WI (US); Carson Hale Thomas, Brookfield, WI (US); Gopal B. Avinash, New Berlin, WI (US); Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 84 days.

(21) Appl. No.: 10/766,362

(22) Filed: Jan. 28, 2004

(65) Prior Publication Data

US 2005/0163278 A1 Jul. 28, 2005

(51) Int. Cl.
*A61B 6/03* (2006.01)
(52) U.S. Cl. ............... 378/8; 378/62; 378/901
(58) Field of Classification Search .......... 378/4, 378/8, 15, 19, 62, 901; 382/131
See application file for complete search history.

(56) References Cited

U.S. PATENT DOCUMENTS

| 5,331,550 | A | * | 7/1994 | Stafford et al. ............. 382/128 |
| 5,838,815 | A | * | 11/1998 | Gur et al. .................... 382/128 |
| 5,987,345 | A | | 11/1999 | Engelmann et al. |
| 6,266,435 | B1 | * | 7/2001 | Wang ......................... 382/132 |
| 6,453,058 | B1 | | 9/2002 | Murthy et al. |
| 6,574,304 | B1 | * | 6/2003 | Hsieh et al. .................. 378/62 |
| 2002/0164061 | A1 | * | 11/2002 | Paik et al. ................... 382/131 |
| 2003/0194115 | A1 | * | 10/2003 | Kaufhold et al. ........... 382/128 |
| 2003/0215120 | A1 | * | 11/2003 | Uppaluri et al. ............ 382/128 |

* cited by examiner

*Primary Examiner*—David V Bruce
(74) *Attorney, Agent, or Firm*—Carl B. Horton, Esq.; Armstrong Teasdale LLP

(57) ABSTRACT

A method for detecting an anomaly includes performing a computed tomography (CT) scout scan to obtain data, and supplying the obtained data to a radiographic computer aided detection (CAD) algorithm.

24 Claims, 7 Drawing Sheets

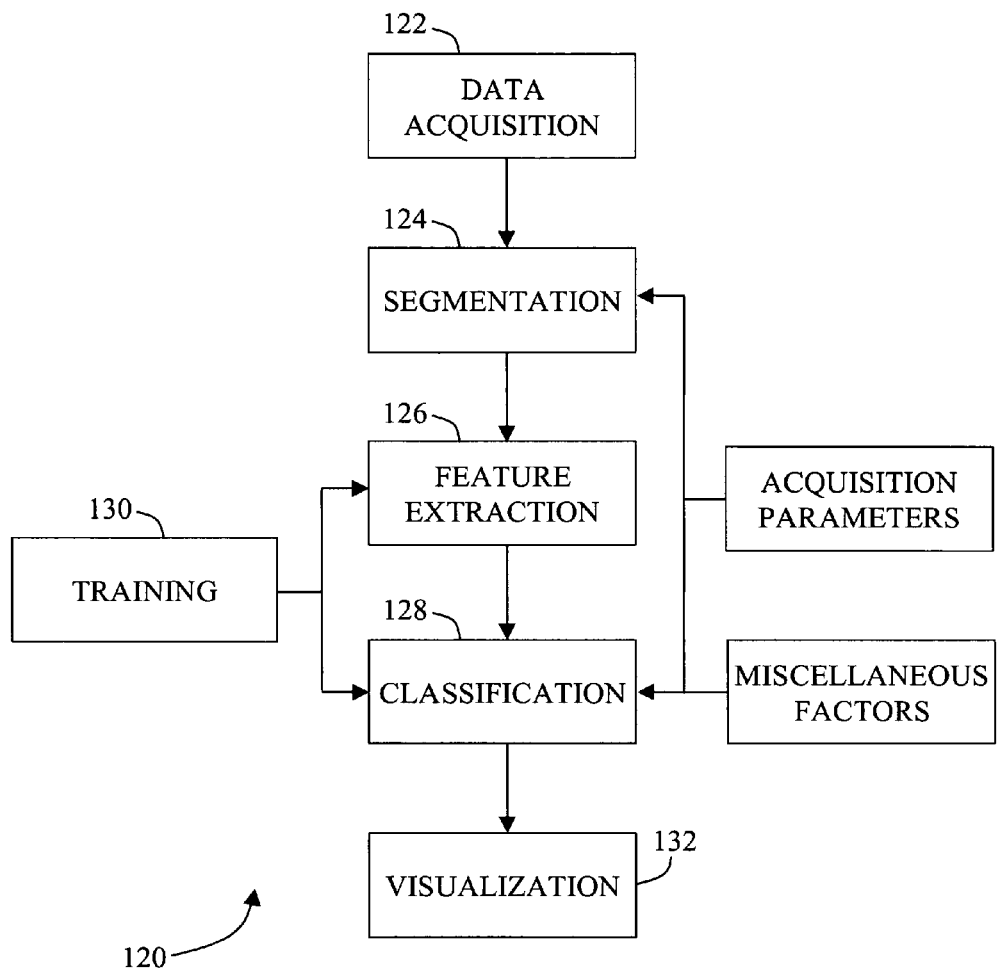
FIG. 7 Schematic of CAD process.

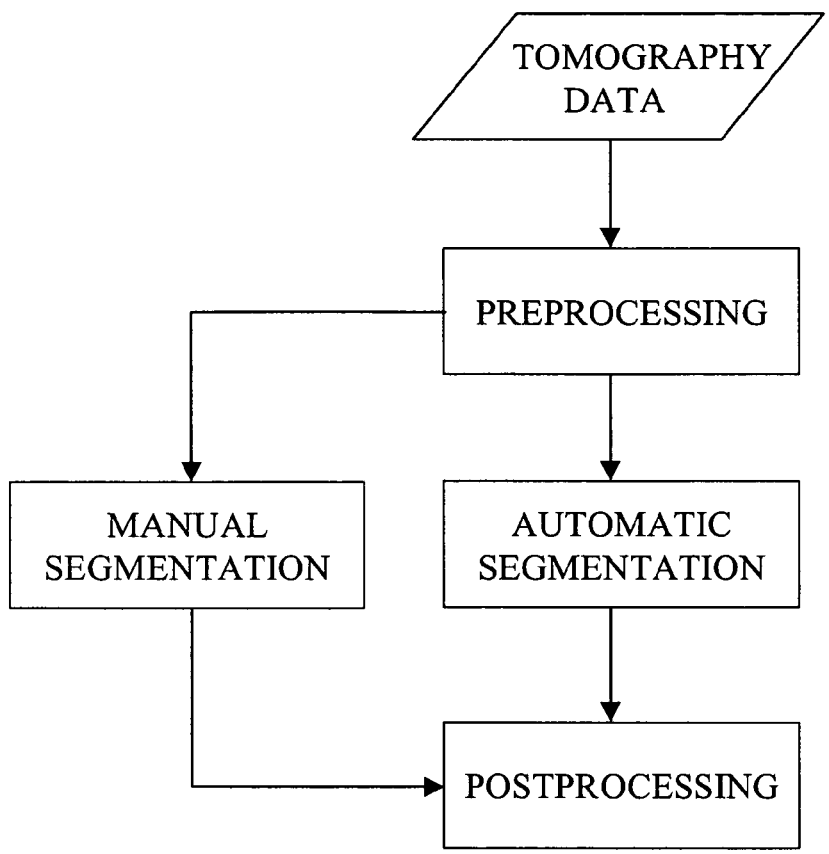
FIG. 8 Segmentation process for data.

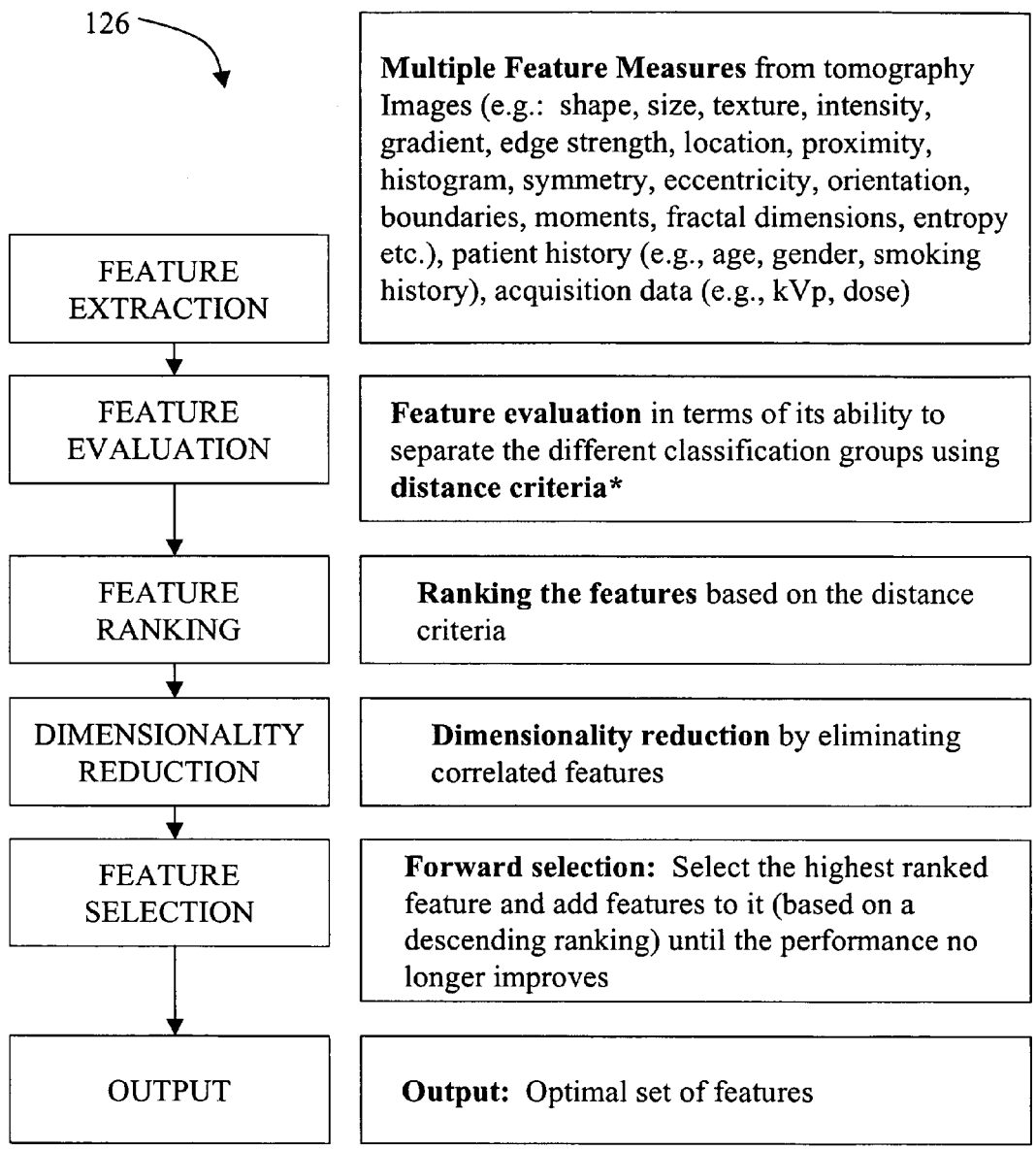
FIG. 9 Feature selection process for data.
*Several different distance criteria can be used: Divergence, Bhattacharya distance, Mahalanobis distance. These techniques are described in standard textbooks including: K. Fukanaga, Introduction to Statistical Pattern Recognition. Academic Press, 2nd ed., 1990.

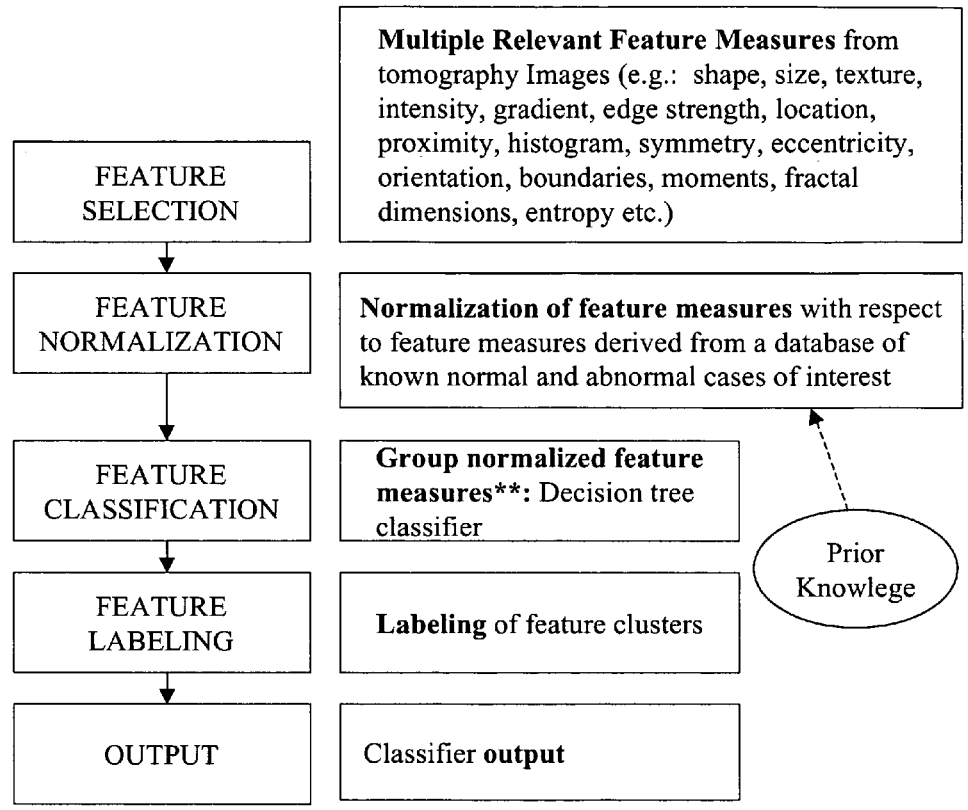

FIG. 10 Feature classification process for tomographic data.

**Several different methods can be used: Decision tree anaylsis, discriminant function analysis, Bayes' minimum-risk method, clustering techniques, similarity measure approach. These techniques are described in standard textbooks including: Fundamentals of digital image processing by Anil K. Jain, Prentice Hall (1988).

METHODS AND APPARATUS FOR ANOMALY DETECTION

BACKGROUND OF THE INVENTION

This invention relates generally to methods and apparatus for computed tomography (CT), and more particularly to methods and apparatus that provide for anomaly detection.

Lung cancer is a disease that is responsible for 28% of all cancer deaths in the U.S., or 157,000 deaths per year for every 165,000 diagnosed. Also, lung cancer patients have an increased survival rate if the disease is detected early. Computed Tomography (CT) is a useful technology to use for cancer detection as it provides high resolution, high throughput, and consistent image quality. However, CT is tends to find many indeterminate anomalies (e.g., nodules) that are difficult for a radiologist to classify.

One medical imaging modality different from Computed Tomography that is also used to detect and classify lung nodules is Radiography. Computed Aided Detection (CAD) algorithms have been developed for Radiography which have empirically shown to improve detection of anomalies such as lung nodules.

BRIEF DESCRIPTION OF THE INVENTION

In one aspect, a method for detecting an anomaly is provided. The method includes performing a computed tomography (CT) scout scan to obtain data, and supplying the obtained data to a radiographic computer aided detection (CAD) algorithm.

In another aspect, a method for detecting an anomaly includes performing a computed tomography (CT) volumetric scan to acquire CT data, generating at least one Digitally Reconstructed Radiograph (DRR) from the acquired CT data, and providing the DRR to a radiographic computer aided detection (CAD) algorithm.

In another aspect, a Computed Tomography system is provided. The system includes an x-ray source, an x-ray detector, and a computer operationally coupled to the x-ray source and the detector. The computer is configured to execute a radiographic Computer Aided Detection (CAD) algorithm on data derived from a first CT scan of an object.

In still another aspect, a computer readable medium encoded with a program is configured to instruct a computer to execute a radiographic Computer Aided Detection (CAD) algorithm on data derived from a CT scan of an object.

In yet another aspect, a method of displaying data is provided. The method includes obtaining an x-ray projection image, supplying the obtained x-ray projection image to a computer aided detection (CAD) algorithm, and displaying results of the CAD algorithm on at least one of a Computed Tomography (CT) scout image and a Digitally Reconstructed Radiograph (DRR).

In one aspect, a method for detecting an anomaly includes performing a volumetric CT scan of an object, generating at least one digitally reconstructed radiograph (DRR) from the volumetric CT scan, and supplying the DRR to a radiographic computer aided detection (CAD) algorithm.

In another aspect, a method for detecting an anomaly includes performing a volumetric CT scan of an object to obtain CT data, registering results from a CAD algorithm regarding x-ray projection data of the object with the obtained CT data, and displaying the registered x-ray projection data with the CT data.

In still another aspect, a method for detecting an anomaly includes obtaining an x-ray projection of an object, registering results from a CAD algorithm regarding CT data of the object with the obtained x-ray projection, and displaying the registered CT data with the x-ray projection.

In yet another aspect, a method for detecting an anomaly includes performing a volumetric CT scan of an object to obtain CT data, obtaining an x-ray projection of the object, supplying the CT data to a CAD algorithm to obtain CT CAD results, supplying the x-ray projection to a CAD algorithm to obtain x-ray CAD results, and displaying the CT CAD results with the x-ray CAD results in a combined display.

In one aspect, a computer readable medium is embedded with a program configured to instruct a computer to receive CT data regarding a volumetric CT scan of an object, receive an x-ray projection of the object, perform a CAD analysis of the received CT data to generate CT CAD results, perform a CAD analysis of the received x-ray projection to generate x-ray CAD results, and combine the CT CAD results with the x-ray CAD results.

BRIEF DESCRIPTION OF THE DRAWINGS

FIG. 7 illustrates an exemplary computer-aided detection (CAD) process.

FIG. 8 illustrates the segmentation module shown in FIG. 7.

FIG. 9 illustrates the feature extraction module shown in FIG. 7.

FIG. 10 illustrates the classification module shown in FIG. 7.

DETAILED DESCRIPTION OF THE INVENTION

Figure 1:
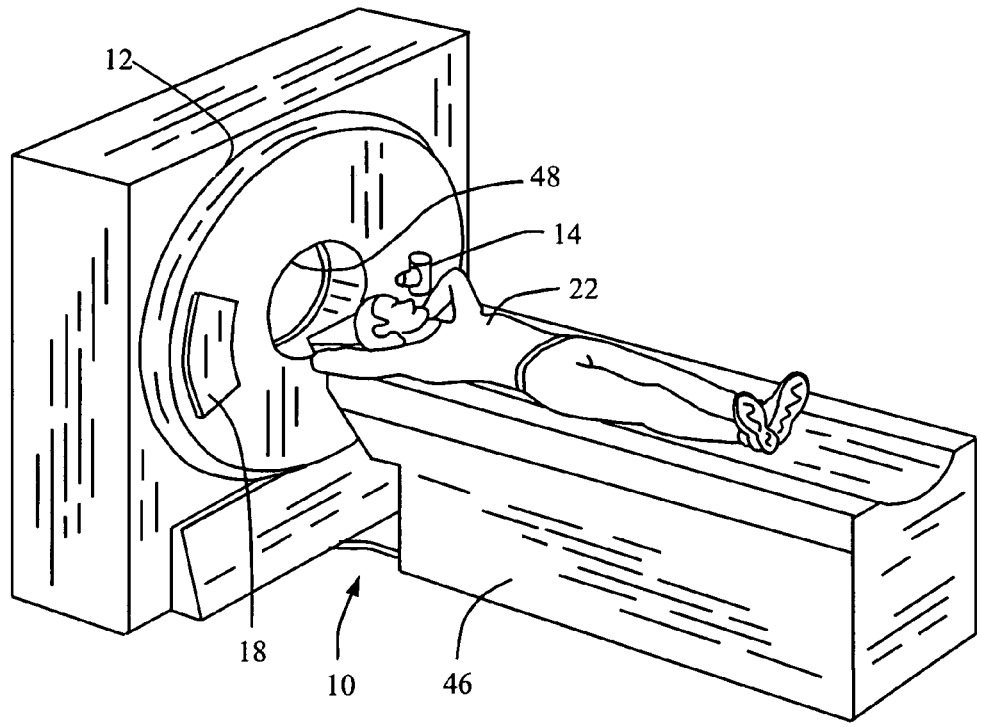
FIG. 1 is a pictorial view of a CT imaging system embodiment.

There is herein provided methods and apparatus useful for Computed Tomography (CT). The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 2:
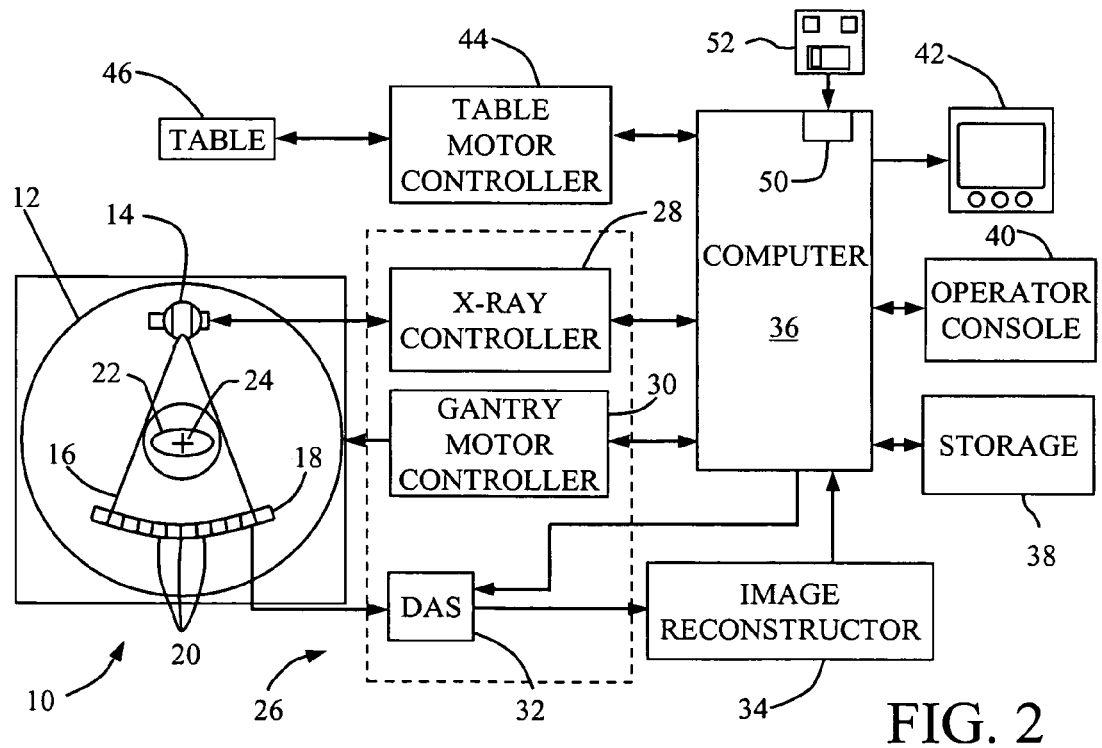
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown in FIGS. 1 and 2) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via a console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center.

Figure 3:
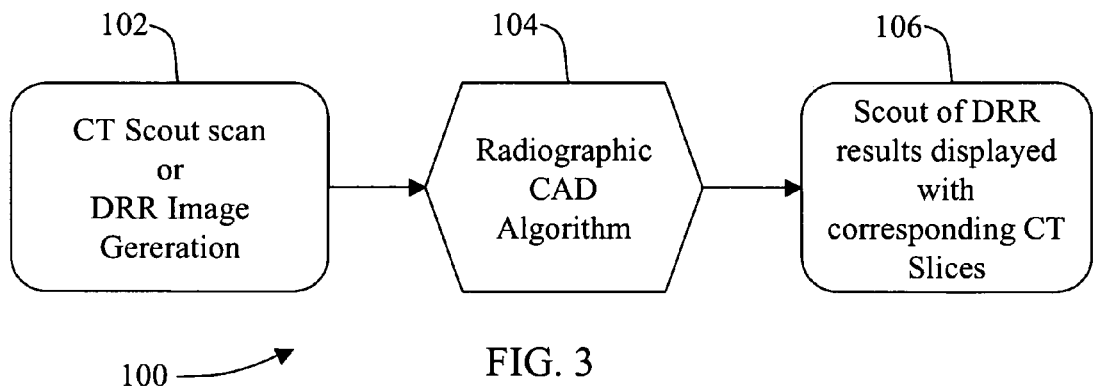
FIG. 3 illustrates a method for detecting an anomaly.

FIG. 3 illustrates a method 100 for detecting an anomaly. Method 100 includes performing 102 a CT scout scan or generating a Digitally Reconstructed Radiograph (DRR) from a CT volume scan, and providing 104 the scout data or the DRR respectively to a radiographic Computer Aided Detection (CAD) algorithm. As used herein, the terms CT scout scan and CT scout data broadly refers to all data acquisitions and the data acquired wherein gantry 12 is stationary and table 46 is moved. There are many suitable 2D CAD algorithms suitable for use as described and one example of a suitable radiographic CAD is RapidScreen commercially available from Deus Technologies of Rockford, Md. Of course other CAD algorithms including non-commercially available CAD algorithms are also suitable. Results from the radiographic CAD are displayed 106 to a user with corresponding CT slice(s). In one embodiment, the results from the CAD algorithm is used by computer 36 to select which axial CT slices to display to the user (e.g., a Radiologist). In one embodiment, the results from the CAD algorithm are used by computer 36 and additional slices around a detected nodule are collected.

Figure 4:
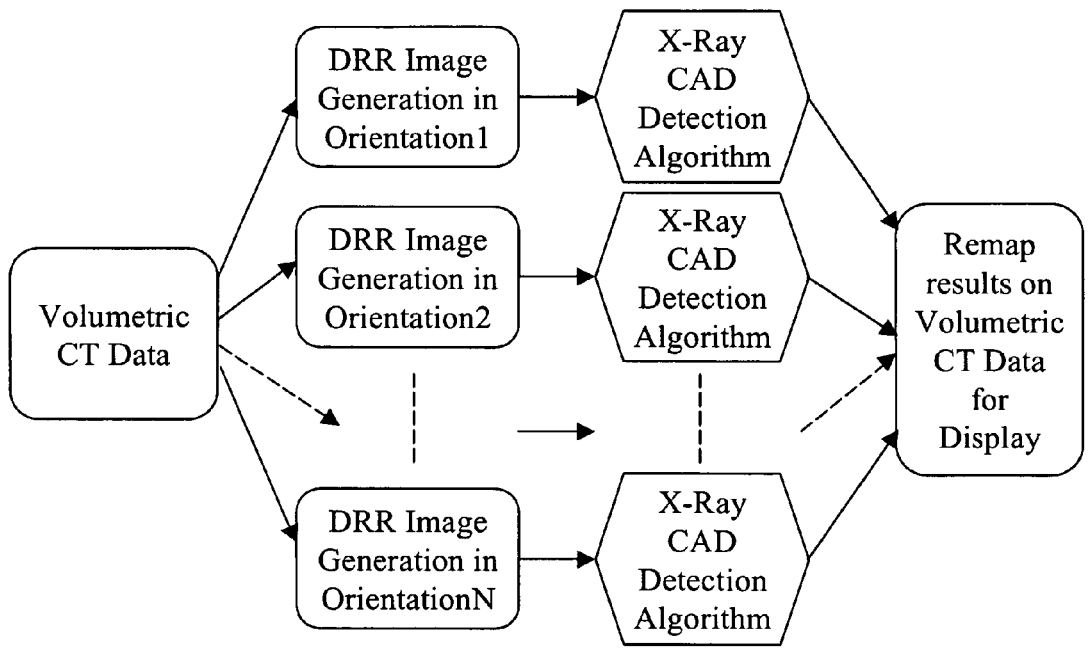
FIG. 4 illustrates generating a plurality of Digitally Reconstructed Radiograph images in multiple orientations from volumetric CT data.

FIG. 4 illustrates generating a plurality of DRR images in multiple orientations from volumetric CT data. The DRR images are provided to the radiographic CAD, and results from the radiographic CAD are remapped on the volumetric CT data for displaying to the user.

Figure 5:
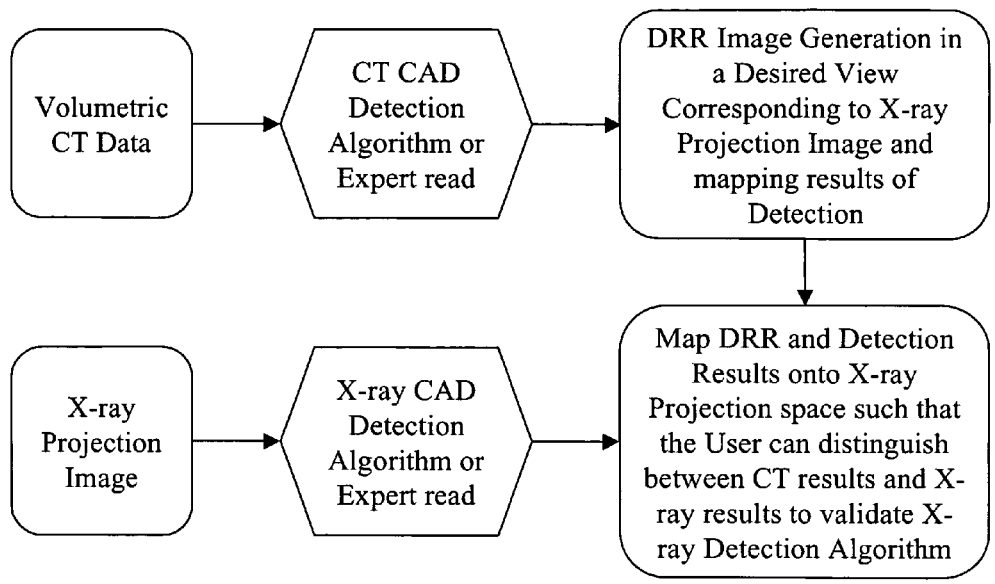
FIG. 5 illustrates a method of validating the radiographic CAD.

FIG. 5 illustrates a method of validating the radiographic CAD. A volumetric CT scan of an object of interest is made to generate volumetric CT data. An x-ray projection image of the object is also generated. The volumetric CT data is provided to a CT CAD algorithm or to a user for visual detection of an anomaly such as a lung nodule. A DRR image is generated which corresponds to the x-ray projection image. The x-ray projection image is provided to an x-ray CAD (i.e., the radiographic CAD) or to a user for visual detection of anomalies. Results from the CT CAD or from the user's visual inspection of the CT slice corresponding to the x-ray projection image, and the DRR are mapped onto the x-ray projection space such that the user can distinguish between CT results and x-ray results to validate the radiographic CAD. If the confidence level of the second set of results is lower than the threshold, then a third CT scan can be performed, and so forth.

Figure 6:
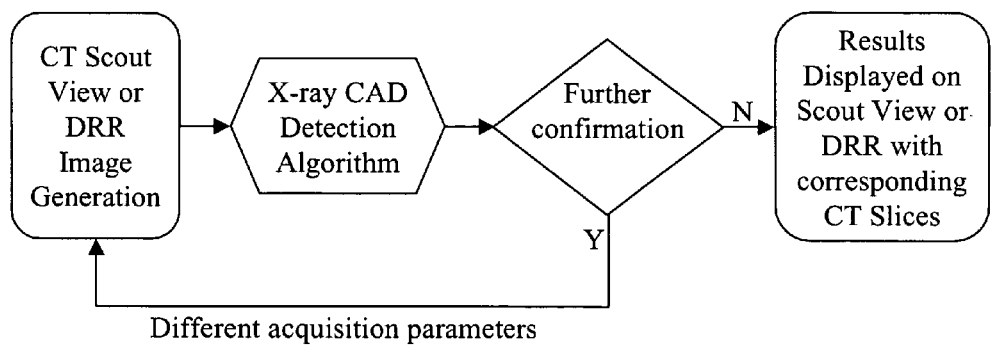
FIG. 6 illustrates an embodiment in which the radiographic CAD results include a confidence level which is utilized to determine if additional scans are performed.

FIG. 6 illustrates an embodiment in which the radiographic CAD results include a confidence level which is utilized to determine if additional scans are performed. A first scan of the object is performed, wherein the first scan is either a scout scan or a CT volumetric scan, and CT scout data or a DRR image generated from CT volumetric data respectively is provided to the radiographic CAD as explained above. The results from the radiographic CAD include a confidence level. The confidence level is compared to a threshold, and a second scan with acquisition parameters different from the first scan is performed when the confidence level is less than the threshold. Typically the first and second scans are both scout scans or both CT volumetric scans, but in one embodiment, the first scan is a scout scan and the second scan is a volumetric CT scan. Alternatively, the first scan is a volumetric CT scan and the second scan is a scout scan.

FIG. 7 illustrates an exemplary computer-aided detection (CAD) process 120. CAD 120 includes several modules regarding data sources 122, segmentation 124, optimal feature selection or extraction 126, classification 128, training 130, and visualization 132. The data from source 122 is successively passed through segmentation module 124, feature extraction module 126, optional classification module 128, and visualization module 132.

Data acquisition module 122 receives data from a combination of one or more sources. The sources include image acquisition system information from a tomographic data source, diagnostic tomographic data (e.g. raw data in projection or Radon domain, single or multiple reconstructed two-dimensional images ('slices' of the patient) or a three-dimensional reconstructed volumetric image data set), and non-image information databases (e.g. patient history).

FIG. 8 illustrates segmentation module 124 shown in FIG. 7 wherein a region of interest (ROI) can be defined to calculate features in the tomographic data. The region of interest can be defined in several ways including using the entire data set or using a part of the data, such as a candidate region in a specific region. Several techniques or their combinations can be used for this purpose including but not limited to iterative thresholding, k-means segmentation, edge detection, edge linking, curve fitting, curve smoothing, 2D/3D morphological filtering, region growing, fuzzy clustering, image/volume measurements, heuristics, knowledge-based rules, decision trees, neural networks. The segmentation of the region of interest can be performed either manually and/or automatically, as depicted in FIG. 8. The manual segmentation involves displaying the data and a user delineating the region using a mouse or any other suitable interface (e.g. touch screen, eye-tracking, voice commands). An automated segmentation algorithm can use prior knowledge such as the shape and size of a mass to automatically delineate the area of interest. A semi-automated method which is the combination of the above two methods may also be used. Therefore, as used herein the term module refers to a section of computer code which performs a specific task as well as a manual process to perform a specific task.

FIG. 9 illustrates feature extraction module 126 shown in FIG. 7. Feature extraction 126 includes performing computations on the data sources. Multiple feature measures can be extracted from the image-based data using region of interest statistics such as shape, size, density, and curvature. For projection space data, features such as location, shape, or size of feature projection in a view or location consistency from view-to-view may be extracted from the dataset. On acquisition-based and patient-based data, the data themselves may serve as the features.

FIG. 10 illustrates classification module 128 shown in FIG. 7. Once the features are computed as illustrated in FIG. 9, a pre-trained classification algorithm, as described in FIG. 10, can be used to categorize the regions of interest into normal and abnormal lesions. Bayesian classifiers, neural networks, rule-based methods or fuzzy logic can be used for classification. It should be noted here that CAD can be performed once by incorporating features from all data or can be performed in parallel. The parallel operation would involve performing CAD operations individually on each data and combining the results of all CAD operations (AND, OR operation or a combination of both). In addition, CAD operations to detect multiple diseases can be performed in series or parallel.

Prior to classification of masses using CAD system 120, prior knowledge from training can be incorporated. The training phase involves the computation of several candidate features on known samples of normal and abnormal lesions. A feature selection algorithm is then employed to sort through the candidate features and select only the useful ones and remove those that provide no information or redundant information. This decision is based on classification results with different combinations of candidate features. The feature selection algorithm is also used to reduce the dimensionality from a practical standpoint because the computation time is very large if the number of features to compute is large. Thus, a feature set is derived that can optimally discriminate normal lesion from abnormal lesion. This optimal feature set is extracted on the regions of interest in the CAD process. Optimal feature selection can be performed using a well-known distance measure including divergence measure, Bhattacharya distance, Mahalanobis distance etc.

Regarding Visualization 132, one embodiment enables the use of tomography image data for review by human or machine observers. CAD techniques can operate on one or all of the data, and display the results on each kind of data, or synthesize the results for display onto a single data. This provides the benefit of improving CAD performance by simplifying the segmentation process, while not increasing the quantity or type of data to be reviewed.

Following identification and classification of a suspicious candidate lesion, the candidate lesion location and characteristics are displayed to a reviewer of the data. In certain CAD applications this is done through the superposition of a marker (e.g. arrow or circle) near or around the suspicious lesion. In other cases CAD affords the ability to display computer detected (and possibly diagnosed) markers on any of the multiple data. In this way, the reviewer may view only a single data upon which results from an array of CAD operations can be superimposed (defined by a unique segmentation (ROI), feature extraction, and classification procedure) would result in a unique marker style (e.g. different color).

Exemplary embodiments are described above in detail. The apparatus and methods are not limited to the specific embodiments described herein, but rather, components of each assembly and/or method may be utilized independently and separately from other components described herein. One technical effect is to provide additional data acquisition when the confidence level is low (e.g., below a predetermined threshold). Other technical effects include the display of CT data with results from a radiographic CAD in a single image to facilitate identification and/classification of an anomaly such as a lung nodule.

While the invention has been described in terms of various specific embodiments, those skilled in the art will recognize that the invention can be practiced with modification within the spirit and scope of the claims.

What is claimed is:

1. A method for detecting an anomaly, said method comprising:
   performing a computed tomography (CT) scout scan to obtain data; and
   supplying the obtained data to a radiographic computer aided detection (CAD) algorithm.

2. A method in accordance with claim 1 further comprising:
   displaying results from the CAD algorithm to a user; and
   displaying a CT scout image generated from the obtained data to the user.

3. A method in accordance with claim 1 further comprising:
   determining a confidence level of the CAD algorithm;
   comparing the determined confidence level to a threshold; and
   performing a second CT scout scan when the determined confidence level is less than the threshold.

4. A method in accordance with claim 1 further comprising:
   determining a confidence level of the CAD algorithm;
   comparing the determined confidence level to a threshold;
   performing a volumetric CT scan when the determined confidence level is less than the threshold;
   generating at least one Digitally Reconstructed Radiograph (DRR) from the volumetric CT scan; and supplying the DRR to the radiographic CAD algorithm.

5. A method in accordance with claim 1 further comprising:
   determining a confidence level of the CAD algorithm;
   comparing the determined confidence level to a threshold;
   performing a volumetric CT scan when the determined confidence level is less than the threshold;
   generating at least one Digitally Reconstructed Radiograph (DRR) from the volumetric CT scan; and
   displaying the DRR.

6. A method in accordance with claim 4 further comprising
   acquiring an x-ray projection image; and
   mapping the DRR and results from the radiographic CAD algorithm onto an x-ray projection space.

7. A method for detecting an anomaly, said method comprising:
   performing a computed tomography (CT) volumetric scan to acquire CT data;
   generating at least one Digitally Reconstructed Radiograph (DRR) from the acquired CT data;
   providing the DRR to a radiographic computer aided detection (CAD) algorithm; determining a confidence level of the CAD algorithm;
   comparing the determined confidence level to a threshold;
   performing a second volumetric CT scan when the determined confidence level is less than the threshold;
   generating at least one Digitally Reconstructed Radiograph (DRR) from the second volumetric CT scan; and
   providing the DRR from the second volumetric CT scan to the radiographic CAD algorithm.

8. A method in accordance with claim 7 further comprising:
   acquiring an x-ray projection image; and
   mapping the DRR and results from the radiographic CAD algorithm onto an x-ray projection space.

9. A method in accordance with claim 7 further comprising displaying results from the radiographic CAD algorithm with a corresponding CT slice.

10. A method in accordance with claim 7 further comprising:
    acquiring an x-ray projection image; and
    map the DRR from the second volumetric CT scan and results from the radiographic CAD algorithm regarding the DRR from the second volumetric CT scan onto an x-ray projection space.

11. A Computed Tomography system comprising:
    an x-ray source;
    an x-ray detector; and
    a computer operationally coupled to said x-ray source and said detector, said computer configured to:
    execute a radiographic Computer Aided Detection (CAD) algorithm on Digitally Reconstructed Radiograph (DRR) data derived from a first CT scan of an object;
    perform a scout scan of the object using said source and detector to generate CT scout scan data; and
    execute the radiographic CAD algorithm on the generated CT scout scan data.

12. A system in accordance with claim 11, wherein to execute a radiographic CAD algorithm said computer further configured to:
    generate at least one Digitally Reconstructed Radiograph (DRR) from CT data; and
    execute the radiographic CAD algorithm on the generated DRR.

13. A system in accordance with claim 11, wherein said computer further configured to:
 compare a confidence level of the radiographic CAD algorithm with a predetermined threshold; and
 perform a second CT scan of the object when the confidence level is below the predetermined threshold.

14. A system in accordance with claim 11, wherein to execute a radiographic CAD algorithm, said computer further configured to:
 perform a volumetric CT scan of the object to generate volumetric CT data;
 generate a plurality of Digitally Reconstructed Radiographs (DRR) each in a different orientation;
 execute the radiographic CAD on each DRR to obtain results;
 map the obtained results on the volumetric CT data; and
 display the volumetric CT data including the mapped results.

15. A system in accordance with claim 13, wherein to perform a second CT scan said computer further configured to:
 perform a volumetric CT scan of the object to generate volumetric CT data;
 generate a plurality of Digitally Reconstructed Radiographs (DRR) each in a different orientation;
 execute the radiographic CAD on each DRR to obtain results;
 map the obtained results on the volumetric CT data; and
 display the volumetric CT data including the mapped results.

16. A system in accordance with claim 15, wherein to execute a radiographic Computer Aided Detection (CAD) algorithm, said computer configured to execute a radiographic Computer Aided Detection (CAD) algorithm on data derived from a first CT scan of an object, wherein the first CT scan comprises a CT scout scan.

17. A system in accordance with claim 15, wherein to execute a radiographic Computer Aided Detection (CAD) algorithm, said computer configured to execute a radiographic Computer Aided Detection (CAD) algorithm on data derived from a first CT scan of an object, wherein the first CT scan comprises a CT volumetric scan.

18. A computer readable medium encoded with a program configured to instruct a computer to perform a method for executing a radiographic Computer Aided Detection (CAD) algorithm on Digitally Reconstructed Radiograph (DRR) data derived from a CT scan of an object, said method comprising:
 obtaining an x-ray projection image;
 supplying the obtained x-ray projection image to a computer aided detection (CAD) algorithm;
 displaying results of the CAD algorithm on at least one of a Computed Tomography (CT) scout image and a Digitally Reconstructed Radiograph (DRR);
 supplying the CT scout image to the computer aided detection (CAD) algorithm;
 registering results from the CAD algorithm regarding the CT scout image with results from the CAD algorithm regarding the x-ray projection image; and
 displaying the registered results regarding both the CT scout image and the x-ray projection image in a combined display.

19. A method in accordance with claim 18 wherein said displaying comprises displaying the registered results regarding both the CT scout image and the x-ray projection image in a combined display such that a user can differentiate the results from the results from the CAD algorithm regarding the CT scout image from the results from the CAD algorithm regarding the x-ray projection image.

20. A method for detecting an anomaly, said method comprising:
 performing a volumetric CT scan of an object;
 generating at least one digitally reconstructed radiograph (DRR) from the volumetric CT scan; and
 supplying the DRR to a radiographic computer aided detection (CAD) algorithm;
 determining a confidence level of the CAD algorithm;
 iteratively performing a volumetric CT scan, generating at least one DRR, providing the DRR to the radiographic CAD algorithm, and determining a confidence level of the results until the confidence level exceeds a threshold.

21. A method for detecting an anomaly, said method comprising:
 performing a volumetric CT scan of an object to obtain CT data;
 obtaining an x-ray projection of the object;
 supplying the CT data to a CAD algorithm to obtain CT CAD results;
 supplying the x-ray projection to a CAD algorithm to obtain x-ray CAD results; and
 displaying the CT CAD results with the x-ray CAD results in a combined display.

22. A method in accordance with claim 21 wherein said displaying comprises displaying the CT CAD results with the x-ray CAD results in a combined display such that a user can differentiate the CT CAD results from the x-ray CAD results.

23. A method in accordance with claim 21 wherein supplying the CT data to a CAD algorithm to obtain CT CAD results comprises:
 generating at least one digitally reconstructed radiograph (DRR) from the volumetric CT scan; and
 supplying the DRR to a radiographic computer aided detection (CAD) algorithm to obtain CT CAD results.

24. A computer readable medium embedded with a program configured to instruct a computer to:
 receive CT data regarding a volumetric CT scan of an object;
 receive an x-ray projection of the object;
 perform a CAD analysis of the received CT data to generate CT CAD results;
 perform a CAD analysis of the received x-ray projection to generate x-ray CAD results; and
 combine the CT CAD results with the x-ray CAD results.

* * * * *

UNITED STATES PATENT AND TRADEMARK OFFICE
CERTIFICATE OF CORRECTION

PATENT NO. : 7,072,435 B2
APPLICATION NO. : 10/766362
DATED : July 4, 2006
INVENTOR(S) : Metz et al.

It is certified that error appears in the above-identified patent and that said Letters Patent is hereby corrected as shown below:

Claim 12, column 8, line 61, delete "at least one" and insert therefor --a plurality of--.
      Claim 12, column 8, line 61, delete "Radiograph" and insert therefor --Radiographs--.
      Claim 19, column 10, line 4, delete "A method" and insert therefor --The method--.

Signed and Sealed this

Twenty-ninth Day of July, 2008

JON W. DUDAS
*Director of the United States Patent and Trademark Office*